US010080728B2

United States Patent
Tets et al.

(10) Patent No.: US 10,080,728 B2
(45) Date of Patent: Sep. 25, 2018

(54) HEMOSTATIC AGENT

(71) Applicants: Viktor Veniaminovich Tets, St. Petersburg (RU); Georgy Viktorovich Tets, St. Petersburg (RU)

(72) Inventors: Viktor Veniaminovich Tets, St. Petersburg (RU); Georgy Viktorovich Tets, St. Petersburg (RU); Konstantin Andreevich Krasnov, St. Petersburg (RU)

(73) Assignees: Viktor Veniaminovich Tets, Saint-Petersburg (RU); Georgy Viktorovich Tets, Saint-Petersburg (RU)

( * ) Notice: Subject to any disclaimer, the term of this patent is extended or adjusted under 35 U.S.C. 154(b) by 0 days.

(21) Appl. No.: 15/545,169

(22) PCT Filed: Apr. 20, 2015

(86) PCT No.: PCT/RU2015/000253
§ 371 (c)(1),
(2) Date: Jul. 20, 2017

(87) PCT Pub. No.: WO2016/118043
PCT Pub. Date: Jul. 28, 2016

(65) Prior Publication Data
US 2018/0008560 A1      Jan. 11, 2018

(30) Foreign Application Priority Data

Jan. 20, 2015   (RU) ................................ 2015101640

(51) Int. Cl.
| A61K 31/155 | (2006.01) |
| A61K 9/06 | (2006.01) |
| A61K 9/08 | (2006.01) |
| A61L 15/20 | (2006.01) |
| A61L 15/44 | (2006.01) |
| A61L 29/08 | (2006.01) |
| A61L 29/16 | (2006.01) |
| A61K 9/00 | (2006.01) |
| A61L 17/00 | (2006.01) |

(52) U.S. Cl.
CPC .......... *A61K 31/155* (2013.01); *A61K 9/0031* (2013.01); *A61K 9/0034* (2013.01); *A61K 9/0048* (2013.01); *A61K 9/06* (2013.01); *A61K 9/08* (2013.01); *A61L 15/20* (2013.01); *A61L 15/44* (2013.01); *A61L 17/005* (2013.01); *A61L 29/08* (2013.01); *A61L 29/16* (2013.01); *A61L 2300/208* (2013.01); *A61L 2400/04* (2013.01)

(58) Field of Classification Search
CPC .. A61K 31/155; A61K 9/0031; A61K 9/0034; A61K 9/0048; A61K 9/06; A61K 9/08; A61L 15/20; A61L 15/44; A61L 17/005; A61L 29/08; A61L 29/16

USPC ......................................................... 514/632
See application file for complete search history.

(56) References Cited

U.S. PATENT DOCUMENTS

| 8,993,712 | B2 | 3/2015 | Tets et al. |
| 2002/0010150 | A1 | 1/2002 | Cortese et al. |
| 2006/0079503 | A1 | 4/2006 | Schwede et al. |
| 2011/0269936 | A1 | 11/2011 | Tets et al. |
| 2013/0096062 | A1 | 4/2013 | Hedrich et al. |
| 2014/0023714 | A1 | 1/2014 | Gagnieu et al. |

FOREIGN PATENT DOCUMENTS

| RU | 2039735 C1 | 7/1995 |
| RU | 2141452 C1 | 11/1999 |
| RU | 2176523 C2 | 12/2001 |

(Continued)

OTHER PUBLICATIONS

Extended European Search Report Issued in European Patent Application No. 14884461.6, dated Aug. 2, 2017, 8 pages.

(Continued)

*Primary Examiner* — Yevgeny Valenrod
(74) *Attorney, Agent, or Firm* — Troutman Sanders LLP

(57) ABSTRACT

The invention relates to medicine, namely, to the solutions used for hemostasis. The hemostatic agent, which represents a polyammonia methanediamine chloride of the general formula $$H-\left[\begin{array}{c}Cl^- \;\; NH_2^+ \\ \overset{|}{\underset{H}{N}}-\overset{|}{\underset{H}{N}}\end{array}\right]\overset{H}{\underset{}{N}}\left[\begin{array}{c}Cl^- \;\; NH_2^+ \\ \phantom{x}\phantom{xxxxxxx}\underset{H}{N}\end{array}\right]_n\!\!\!\!\!-NH_2$$

where: n=1-20, m=1-10, at that n×m≥8.

The hemostatic agent may be applied in the form of a 0.01-10% aqueous solution. An aqueous solution of the preparation can be used for impregnation of materials used for bleeding arrest, suture material, bandaging material. The hemostatic agent may be used in the composition of a retraction cord, adhesive pastes, vaginal and rectal suppositories, creams, gels, as well as used with microchips that provide slow release of the preparation. The preparation can also be used in eye drops, eye ointments, and lubricants applied to the surface of the catheter. The drug can be used in endodontic treatment, may be injected into a polymer sealer for root canal obturation, as well as locally—by means of electrophoresis. The hemostatic agent may be used in conjunction with a gel based on aluminum sulphate or silver solution, and also with a polysaccharide haemostatic system. An efficient haemostatic preparation ensuring a significant analgetic effect is developed.

20 Claims, No Drawings

(56) References Cited

FOREIGN PATENT DOCUMENTS

| RU | 2176651 C2 | 12/2001 |
| --- | --- | --- |
| RU | 2230734 C1 | 6/2004 |
| RU | 2004135533 A | 7/2005 |
| RU | 2006122738 | 1/2008 |
| RU | 2324478 C2 | 5/2008 |
| RU | 2422137 C1 | 6/2011 |
| RU | 2423359 C1 | 7/2011 |
| RU | 2480227 C2 | 4/2013 |
| RU | 2012130924 A | 1/2014 |
| RU | 2533232 C2 | 11/2014 |
| RU | 2546006 C1 | 4/2015 |
| WO | 1996/28570 A1 | 9/1996 |
| WO | 1999/18232 A1 | 4/1999 |
| WO | 2001/082937 A1 | 11/2001 |
| WO | 20030093249 A1 | 11/2003 |
| WO | 2008008912 A1 | 1/2008 |
| WO | 2011/135577 A1 | 11/2011 |
| WO | 2013/053753 A2 | 4/2013 |

OTHER PUBLICATIONS

Lysytsya a., et al., "The Antiviral Action of Polyhexamethylene Guanidine Derivatives", Journal of Life Sciences (2014), vol. 8, No. 1, pp. 22-26.

Bailey, A. et al., "Virucidal activity of chlorhexidine on strains of Herpesvirus hominis, poliovirus, and adenovirus", Journal Clinical Path. (1972), vol. 25, pp. 76-78.

Denton, G.W. (1991), Chlorhexidine in: Block, S.S., Ed., Disinfection, Sterization, Preservations, 4 Edition, Lea & Fegiber, Philadelphia, 274-289.

European Extended Serach Report Issued in European Patent Appln No. 10822298.5 for PCT/RU2010/000292, dated Nov. 20, 2013, 3 pages.

Extended European Search Report Issued in European Application No. 16167120.1 dated Oct. 27, 2016, 7 pages.

European Extended Serach Report Issued in European Patent Appln No. 13853343.5 for PCT/RU2013/000394, dated Jun. 6, 2016, 6 pages.

International Search Report and Written Opinion Issued in PCT/RU2014/000917, dated Apr. 29, 2015 and English Translation Thereof, 12 pages.

International Search Report and Written Opinion Issued in PCT/RU2015/000253, dated Sep. 10, 2015; and English Translation Thereof, 10 pages.

Translation of the International Search Report and Written Opinion of the International Searching Authority dated Oct. 28, 2010, from corresponding International Application No. PCT/RU2010/000292, 11 pages.

Translation of the International Prelimianry Report on Patentability dated Apr. 11, 2012 from corresponding International Application No. PCT/RU2010/000292, 4 pages.

Wei, Dafu et al., "Structural characterization and antibacterial activity of oligoguanidine (polyhexamethylene guanidine hydrochloride)", Materials Science and Engineering C 29 (2009), pp. 1776-1780.

HEMOSTATIC AGENT

CROSS-REFERENCE TO RELATED APPLICATIONS

This application is a U.S. National Phase of International Patent Application No. PCT/RU2015/000253, filed on Apr. 20, 2015, which published as WO 2016/118043 A1 on Jul. 28, 2016 and claims priority to Russian Patent Application No. 2015101640, filed on Jan. 20, 2015, all of which applications are herein incorporated by reference in their entirety.

TECHNICAL FIELD

The invention relates to medicine, namely, to the solutions used for hemostasis.

BACKGROUND ART

A liquid foaming hemostatic agent containing protein as a foaming component and fibrinogen as the active substance has been commonly known; the preparation may also include a coagulation-accelerating agent, US2014161738 (A1), published on 12 Jun. 2014.

The disadvantage of this solution is the low efficiency of hemostasis, and the lack of analgesic effect.

Another commonly known hemostatic composition is a powder comprising collagen in the form of fibers, and at least one monosaccharide; the composition may also contain a mixture of coagulants and glucosamineglucans, US2014023714 (A1), publ. 23 Jan. 2014.

This solution does not produce an analgesic effect, and in some cases may intensify the pain when applied to the wound.

There is another commonly known hemostatic agent intended mainly for use in dentistry. The composition is a hydrophilic paste comprising % wt: 5-15 aluminum chloride, 2-15 kaolin, 10-20 structurant, 50-70 water, 0-20 humectant; the total amount of water and humectant is 55-75% of the total weight of the composition; US2014348921 (A1), publ. 27 Nov. 2014.

This composition has a satisfactory hemostatic effect, but its use is generally limited to dentistry; the composition does not produce any analgesic effect.

Another commonly known hemostatic agent is Ferric Subsulfate (trade name: AstrinGyn), which is a solution of iron salts 259 mg/g, http://www.drugs.com/ppa/ferric-subsulfate.html, 8 Dec. 2014.

This preparation, which is adopted as a prototype of the claimed invention, has pronounced hemostatic properties at small dimensions of the wound surface, but provides no local anesthetic effect.

SUMMARY OF THE INVENTION

It is an object of the present invention to provide an efficient haemostatic preparation ensuring a significant analgesic effect.

Since the practice of medicine shows that in most cases bleeding is accompanied by pain, the task of creating effective hemostatic drugs with analgesic effect is both important and vital.

According to the invention, the hemostatic agent represents a polyammonia methanediamine chloride of the following general formula:

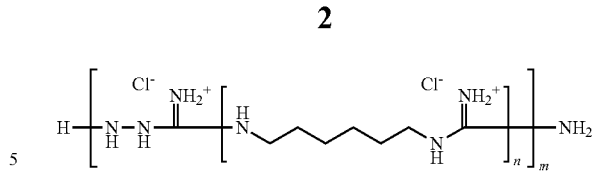

where: $n=1$-$20$, $m=1$-$10$, at that $n \times m \geq 8$.

The hemostatic agent may be applied in the form of a 0.01-10% aqueous solution. An aqueous solution of the preparation can be used for impregnation of materials used for bleeding arrest, suture material, bandaging material. The hemostatic agent may be used in the composition of a retraction cord, adhesive pastes, vaginal and rectal suppositories, creams, gels, as well as used with microchips that provide slow release of the preparation. The preparation can also be used in eye drops, eye ointments, and lubricants applied to the surface of the catheter. The drug can be used in endodontic treatment, may be injected into a polymer sealer for root canal obturation, as well as locally—by means of electrophoresis. The hemostatic agent may be used in conjunction with a gel based on aluminum sulphate or silver solution, and also with a polysaccharide haemostatic system.

The claimed solution was prepared as follows.

EXAMPLE 1

$n=10$, $m=1$.

Into a three-necked 1 liter flask equipped with an inert gas supply tube, a thermometer and a gas outlet tube 95.5 g (1 mole) of hydrochloride aminemethanediamine (46.7 wt. %), and 104.4 g (0.90 mol) of 1.6-diaminohexane (DH) (51.1 wt. %) were introduced, after which the flask was purged with nitrogen. The contents of the flask were heated to 100° C. and stirred until complete dissolution. Then 4.5 g (0.09 mol) of hydrazine hydrate (HH) (2.2 wt. %) were added, the solution was stirred and placed into an air thermostat, and the gas outlet tube was connected to the receiver for ammonia capturing. Then, while purging with nitrogen at a rate of 30-40 ml/min, the reaction mixture was heated with gradual removal of water and ammonia for 1 hour adjusting the temperature of the mass to the constant reaction temperature of 190° C. Reaction temperature was maintained for 30 minutes, while the system was purged with nitrogen. Thereafter, the system was cooled to 160° C. and the hot syrupy mixture was poured onto a metal pan and cooled, obtaining 169.9 of product in the form of a solid, almost colorless transparent substance.

EXAMPLE 2

The hemostatic agent was prepared analogously to Example 1, with $n=5$, $m=2$, DH=0.85 mole, HH=0.17 mole.

EXAMPLE 3

The hemostatic agent was prepared analogously to Example 1, with $n=10$, $m=2$, DH=0.9 mole, HH=0.09 mole.

EXAMPLE 4

The hemostatic agent was prepared analogously to Example 1, with $n=10$, $m=5$, DH=0.9 mole, HH=0.09 mole.

EXAMPLE 5

The hemostatic agent was prepared analogously to Example 1, with $n=15$, $m=10$, DH=0.93 mole, HH=0.063 mole. The reaction temperature and the holding time according to Examples 1-5 are given in Table 1.

The resulting polymer is non-stereoregular, i.e. the mutual arrangement of alternating components of hydrazine and 1.6 of diamine-hexane in the polymer chain may be arbitrary. But the average proportion of these components determined by the proportion of the initial reagents has a constant value in each example. The resulting material has a nanostructure.

The nanostructure is determined by the methods of dynamic light scattering using a Malvern Instruments Nanosizer Nano-ZS particle size analyzer and a FEI Tecnai G212Cryo12 transmission electron microscope enabling tp cool the samples at the boiling point of liquid nitrogen.

By the dynamic light scattering method was found that at the preparation concentration of 0.05 mg/ml the solution contains globules by the size of 10-15 nm. An electron-microscopic examination also revealed globules by the size of 10-15 nm.

The applicant has not found any sources of information containing data on technical solutions identical to the claimed invention, which enables to conclude that the claimed invention conforms to the criterion "Novelty" (N).

The applicant has not found any sources of information containing data on the technical result achieved by means of the invention, that is providing both an effective hemostatic effect and a significant analgesic effect. This, in the applicant's opinion, indicates that the invention conforms to the criterion "Inventive Step" («IS»).

BRIEF DESCRIPTION OF DRAWINGS

The invention is further explained, by way of detailed description of examples of its embodiments, without any references to drawings.

PREFERRED EMBODIMENT

The effectiveness of the claimed hemostatic agent with analgesic effect is shown in the following examples.

I. Examination of Hemostatic Activity of the Preparation

EXAMPLE 1.1

The influence of the claimed substance on the hemostatic function was examined in rabbits of both sexes weighing 2000-4000 g. The experiments were carried out under general anesthesia. The animals underwent a laparotomy with a section made along the white line of the abdomen. The intestine was exteriorized into the wound and limited by wipes moistened with 0.9% sodium chloride solution (temperature 370° C.), as well as the front surface of the liver. A superficial wound of the liver by the area of 1.5 cm$^2$ and the depth of 0.1 cm was inflicted by means of a razor.

Arrest of the capillary-parenchymal bleeding was carried out by uniform application of a 1% solution or a spray of the claimed substance on the entire area of the wound surface. At that, iron subsulfat was used for comparison of the bleeding arrest time. Hemostatic activity was evaluated by the change of the bleeding intensity. The results are shown in Table 2.

The data in Table 2 show a higher hemostatic activity of the claimed substance in comparison to the prototype.

EXAMPLE 1.2

To evaluate the efficiency of the claimed substance at impregnation of the bandaging material used for hemostasis, a sterile swab was impregnated with a solution of the claimed substance in a concentration of 0.01% to 10%, and then dried. A conventional gauze swab was used for reference in order to compare the bleeding arrest time. An animal model was used in the experiment, as described in Example No. 4. Hemostatic activity was evaluated by the change of the bleeding intensity. The results are shown in Table 3.

The data in Table 3 show a high hemostatic activity of the claimed substance when used for impregnation of materials used for hemostasis. This activity is higher in the claimed substance in comparison with the prototype.

EXAMPLE 1.3

To evaluate the efficiency of the claimed substance at impregnation of suture materials used in surgery, a resorbable suture material (catgut) and a non-resorbable suture material (nylon) were impregnated with a 5% solution of the claimed substance. The same suture material, not impregnated with the claimed substance, was used for reference in order to compare the bleeding arrest time. An animal model (rabbits) was used in the experiment, in which the anesthetized animals underwent an incision (2 cm long and 0.5 cm deep) made in each rabbit's paw. Hemostatic activity was evaluated by the change of the bleeding intensity. The results are shown in Table 4.

The data in Table 4 show a high hemostatic activity of the claimed substance when used for impregnation of suture materials.

EXAMPLE 1.4

Evaluation of the efficiency of the claimed substance was studied when added to various absorbent hemostatic agents for local administration in the form of a solution in a concentration of 0.01% to 10%. Hemostatic agents for local administration, not impregnated with the claimed substance, were used for reference in order to compare the bleeding arrest time: collagen hemostatic sponge, fibrin film комбинированная губка containing sponge fibrinogen and thrombin. An animal model was used in the experiment, as described in Example No. 4.

Hemostatic activity was evaluated by the change of the bleeding intensity. The results are shown in Tables 5-7.

The data in Table 5 show a high hemostatic activity of the claimed substance when used together with a collagen hemostatic sponge. This activity is higher in the claimed substance in comparison with the prototype.

The data in Table 6 show a high hemostatic activity of the claimed substance when used together with a fibrin film.

The data in Table 7 show a high hemostatic activity of the claimed substance when used together with комбинированной губкой a sponge containing fibrinogen and thrombin.

EXAMPLE 1.5

Hemostatic activity of the claimed substance was studied when added to hemostatic polymers in a concentration of 0.01% to 10%. A polysaccharide hemostatic system and a hemostatic material based on cellulose were used for reference in order to compare the bleeding arrest time. An animal model was used in the experiment, as described in Example No. 4. Hemostatic activity was evaluated by the change of the bleeding intensity. The results are shown in Tables 8 and 9.

The data in Table 8 show a high hemostatic activity of the claimed substance when used together with a polysaccharide hemostatic system.

The data in Table 9 show a high hemostatic activity of the claimed substance when used together with a hemostatic material based on cellulose.

EXAMPLE 1.6

Evaluation of efficiency of the claimed substance was studied when used together with a gel based on aluminum sulfate, and a silver nitrate solution (1:200). A gel based on aluminum sulphate or silver nitrate solution (1:200) without addition of the claimed substance was used for comparison of the hemostasis time as a reference (for control). An animal model was used in the experiment, as described in Example No. 4. Hemostatic activity was evaluated by the change of the bleeding intensity. The results are shown in Table 10.

The data in Table 10 show a high hemostatic activity of the claimed substance when used together with a gel based on aluminum sulphate or a silver nitrate solution.

EXAMPLE 1.7

Evaluation of efficiency of the claimed substance was studied when impregnating a retraction cord with it, with the solution concentration of 0.01% to 10%. A retraction cord, not impregnated with the claimed substance, was used as a reference in order to compare the bleeding arrest time. The experiments were carried out on humans from among volunteers who required arrest of bleeding from periodontal pockets, which occurred as a result of a dental treatment. Hemostatic activity was evaluated by the change of the bleeding intensity. The results are shown in Table 11.

The data in Table 11 show a high hemostatic activity of the claimed substance when used together with a retraction cord. This activity is higher in the claimed substance in comparison with the prototype.

EXAMPLE 1.8

Evaluation of efficiency of the claimed substance was studied when applied in concentration of 0.01% to 10% onto bandaging materials or a plaster for application onto the wound surface. A bandaging material or a plaster, not impregnated with the claimed substance, was used as a reference in order to compare the bleeding arrest time. The experiments were carried out in rabbits. The animals were cut with a lancet under local anesthesia; the 2 cm long and 0.5 cm deep incision was made in the rabbits' paws. Hemostatic activity was evaluated by the change of the ultimate bleeding arrest time. The results are shown in Table 12.

The data in Table 12 show a higher hemostatic activity of the claimed substance.

II. Determination of Anesthetic Activity

EXAMPLE 2.1

A study to determine anesthetic activity was carried out in unanesthetized rabbits, which were placed in a special box with a hole to restrain the animal's head. The study was conducted to determine the threshold of sensitivity of the rabbit's eye to a tactile impact. For this purpose, a thin metal wire was used without injuring the cornea. The examined compound and the reference drug (oxybuprocaine) were administered into the conjunctival sac of the rabbit's eye in the form of a 0.5% aqueous solution with the total volume of up to 0.4 ml. Determination of topical anaesthesia was performed starting from the 1st minute of the study. The absence of the blinking reflex for 1 min (100 touches) was considered as an indicator of full anesthesia. Based on the collected data reflecting the changes in corneal sensitivity under the influence of the drugs, the beginning, the duration of complete (100%) anesthesia and the total duration of anesthesia were determined.

The relative activity of the tested compounds was calculated according to the Valet equation. The Rainier index is 852.4 for the claimed preparation and 63.5 for the reference preparation. The duration of anesthesia was 234 minutes for the claimed preparation and 24 min for oxibuprocaine.

EXAMPLE 1.8

Evaluation of the claimed substance's anesthetic activity was studied when dispersing a spray containing 0.01-10% of the preparation, or when applied at a concentration of 0.01% to 10% onto a bandaging material or a plaster for application onto the wound surface. An iron subsulfate solution was used as a reference. For efficiency evaluation the change in the pain sensation intensity on the visual analog scale (VAS) from 0 to 10 points in 1 minute after application of the product and after 2 days in everyday use was used. The results are shown in Table 13.

The data in Table 13 show a high activity of the claimed substance for elimination of pain with soft corn and no analgesic effect in the prototype.

EXAMPLE 2.3

Evaluation of the claimed substance's anesthetic activity to reduce itch at genital candidiasis was studied when applied onto mucosae in the form of a 0.01% to 10% solution or by administering vaginal suppositories containing the claimed substance. To evaluate the efficiency the change in the itch sensation intensity on the Itch Severity Score (ISS) in 1 minute after application/administration of the product and after 5 days in case of everyday administration was used. The results are shown in Table 14.

The data in Table 14 show a high activity of the claimed substance for elimination of mucosae itch and no analgesic effect in the prototype.

EXAMPLE 2.4

Evaluation of efficiency of the claimed substance to reduce pain in lesions of the mucous membranes through the example of aphthous stomatitis. Patients in the control group suffering aphthous stomatitis with severe pain received an adhesive solcoseryl paste, while patients in the other group received a paste containing 0.01% to 10% of the claimed preparation. To evaluate efficiency the change in the pain sensation intensity on the visual analog scale in 1 minute after application of the preparation and after 2 days in case of everyday application was used. The results are shown in Table 15.

The data in Table 15 show a high activity of the claimed substance for elimination of pain in lesions of the mucous membranes.

EXAMPLE 2.5

Evaluation of efficiency of the claimed substance to reduce pain and bleeding in hemorrhoids was studied by administration of rectal suppositories containing the claimed substance. Efficiency of the suppositories in patients with chronic hemorrhoids was studied, as well as in patients with chronic hemorrhoids at stages II and III with a florid pain syndrome. The final result of the treatment was assessed by examination of the patient in 3 and 7 days after beginning of the treatment by three indications on a 3-point scale for each indication. Iron subsulfate suppositories were used as a reference.

The data in Table 16 show a high activity of the claimed substance in treatment of hemorrhoids and lack of therapeutic effect in the prototype by indications of "pain" and "anal itching", as well as a lower efficiency by indication of "hemorrhage".

EXAMPLE 2.6

Evaluation of efficiency of the claimed substance to reduce itch in patients suffering atopic dermatitis, eczema, neurodermatitis or psoriasis were studied when applied to the affected area in the form of a solution in a concentration of 0.01% to 10%, in the form of a cream containing 0.01% to 5% of the preparation, in the form of a 0.01%-5% gel, in the form of 0.01%-5% ointment in the form of application strips with a 0.01%-10% solution of the preparation spread on them. To evaluate the efficiency the change in the itch sensation intensity on the Itch Severity Score (ISS) in 1 minute after application/administration of the product and after 5 days in case of everyday administration was used. The results are shown in Table 17.

The data in Table 17 show a high activity of the claimed substance for elimination of itch in skin diseases.

EXAMPLE 2.7

Evaluation of efficiency of the claimed substance for pain reduction in patients with burns was studied when applied in the form of solution/spray onto the affected areas in a concentration of 0.01% to 10%. To evaluate efficiency the change in the pain sensation intensity on the visual analog scale (VAS) from 0 to 10 points in 1 minute after application/administration of the preparation and after 5 days in case of everyday application was used. The results are shown in Table 18.

The data in Table 18 show a high activity of the claimed substance for elimination of pain in burns.

EXAMPLE 2.8

Evaluation of efficiency of the claimed substance for pain reduction was studied in patients suffering the postoperative pain syndrome. After laparoscopic cholecystectomy the claimed substance was applied onto the affected areas of the patients in the form of a solution/spray in a concentration of 0.01% to 10%. As a comparison preparation for surface anesthesia oxybuprocaine was used. To evaluate efficiency the change in the pain sensation intensity on the visual analog scale (VAS) in 1 minute after application/administration of the preparation and after 2 days in case of everyday application was used. The results are shown in Table 19.

The data in Table 19 show a high activity of the claimed substance for elimination of pain in skin lesions.

EXAMPLE 2.9

Evaluation of efficiency of the claimed substance for pain reduction in angina was studied in patients suffering angina. Patients with severe pain when swallowing were treated with a solution for gargling (or a spray for application onto tonsils) in a concentration of 0.01% to 10%. A 0.9% sodium chloride solution was used as a reference. To evaluate efficiency the change in the pain sensation intensity on the visual analog scale (VAS) in 1 minute after application/administration of the preparation and after 2 days in case of everyday application was used. The results are shown in Table 20.

The data in Table 20 show a high activity of the claimed substance for elimination of pain in angina.

EXAMPLE 2.10

Evaluation of efficiency of the claimed substance for bleeding reduction in endodontic treatment was studied in animals. For this purpose, the dogs underwent a procedure under local anesthesia in which a tooth cavity was opened and the pulp surface was exposed. At the pulp removal a bleeding occurred, which was stopped by means of a solution of the claimed substance in a concentration of 0.01% to 10%, or by means of paper points impregnated with the claimed substance or cotton swabs impregnated with the claimed substance. Animals in the control groups received either 0.9% sodium chloride solution or cotton swabs/paper points without impregnation. The efficiency was evaluated by the change of the ultimate bleeding arrest time. The results are shown in Table 21.

The data in Table 21 show a high activity of the claimed substance for use in endodontic practice.

EXAMPLE 2.11

Evaluation of efficiency of the claimed substance for pain reduction in patients undergoing an endodontic treatment. For this purpose, a polymer sealer for root canal obturation was administered with the claimed substance up to its final concentration of 0.01% to 2%. The control group patients received the polymer sealer for obturation channels. The study included patients who underwent an endodontic treatment for acute exacerbation of chronic pulpitis of molars. To evaluate efficiency the change in the pain sensation intensity (on the visual analog scale (VAS) in 24 and 36 hours after treatment and the drug administration). The results are shown in Table 22.

The data in Table 22 show a high activity of the claimed substance for elimination of pain in endodontic treatment.

EXAMPLE 2.12

Evaluation of efficiency of the claimed substance for pain reduction in inflammatory diseases of the paradentium and gums in patients with the corresponding pain syndrome. Patients rinsed mouth with a 0.01%-10% solution of the preparation or received a 0.01%-10% gel, which was injected into the periodontal pocket or received "chips" with slow release of the active substance contained in a concentration of 0.01% to 10%. A 0.9% sodium chloride solution was used for preparations of the control group. To evaluate efficiency the change in the pain sensation intensity on the visual analog scale (VAS) in 1 minute after application/administration of the preparation and after 2 days in case of everyday application was used. The results are shown in Table 23.

The data in Table 23 show a high activity of the claimed substance for elimination of pain in inflammatory diseases of the paradentium and gums.

EXAMPLE 2.13

Evaluation of efficiency of the claimed substance for pain and bleeding reduction in patients with respiratory diseases (chronic obstructive pulmonary disease, pneumonia, cystic fibrosis, tuberculosis, etc.) and after diagnostic procedures (bronchoscopy, bronchial lavage, etc.).

Patients received a solution of the claimed substance in a concentration of 0.01% to 1% by inhalation using a nebulizer. An iron subsulfate solution was given to the control group patients. The study included patients with chronic obstructive pulmonary disease, who pointed out a growing pain in the chest and the appearance of cough with bloody sputum in the last three days. To evaluate efficiency the change in the pain sensation intensity on the visual analog scale in 1 minute after administration of the preparation and after 5 days in case of everyday single application and the disappearance of traces of blood in the sputum was used.

The presence of blood in the sputum was visually evaluated as follows:
"+++"—A significant amount,
"+"—A moderate amount,
"+"—A small amount,
"−"—absence.

The results are shown in Tables 24 and 25.

The data in Table 24 show a high anesthetic activity of the claimed substance for elimination of pain in various diseases of the respiratory system and the absence of such activity in the prototype (iron subsulphate).

The data in Table 25 show a high hemostatic activity of the claimed substance for reduction of the severity of pulmonary hemorrhage.

EXAMPLE 2.14

Evaluation of efficiency of the claimed substance for pain reduction in patients with diseases of the musculoskeletal system. Patients with arthritis, rheumatism, osteochondrosis were administered a solution of the claimed substance locally, by means of electrophoresis.

The control group patients received a 0.9% sodium chloride solution with the same method of injection. For efficiency evaluation the change in the pain sensation intensity on the visual analog scale (VAS) from 0 to 10 points was used.

The results are shown in Table 26.

EXAMPLE 2.15

Evaluation of efficiency of the claimed substance for pain reduction in patients with lesions of joints in gout. The patients were administered a solution of the claimed substance locally, by means of electrophoresis. The criteria for inclusion of patients into the study were as follows: diagnosis of gout according to ACR criteria (4), age of over 18 years, acute gouty arthritis, the duration of which does not exceed 3 weeks, affection of no more than 4 joints and an informed consent signed by the patient. Further, an evaluation of pain severity as per VAS for 7 days. Computer processing of the results was performed using Statistica package of statistical software, version 6. The control group patients received a 0.9% sodium chloride solution with the same method of injection.

The results are shown in Table 27.

EXAMPLE 2.16

Evaluation of efficiency of the claimed substance for eyeball pain reduction in posttraumatic processes. The claimed substance solution was instilled into the conjunctival sac of patients with various lesions of the eyeball, including after surgery. As a reference, diclofenac eye drops were used. For efficiency evaluation the change in the pain sensation intensity on the visual analog scale (VAS) from 0 to 10 points was used.

The results are shown in Table 28.

EXAMPLE 2.17

Evaluation of the claimed substance efficiency for reduction of bleeding and pain in ENT, upper respiratory and digestive systems pathologies, in the course of instrumentation studies of these systems. Patients with various medical interventions after treatment with haemostatic purpose and pain reduction were treated with the claimed preparation. An iron subsulfate solution was used as a reference. For efficiency evaluation the change in the pain sensation intensity on the visual analog scale (VAS) from 0 to 10 points was used.

The results are shown in Tables 29 and 30.

The data in Table 29-30 show a high hemostatic activity of the claimed substance; in addition, the claimed substance significantly reduces pain, unlike the prototype.

INDUSTRIAL APPLICABILITY

The invention can be implemented using common constructional materials and equipment, resulting, according to the applicant's opinion, in compliance of the invention with the "Industrial Applicability" ("IA") patentability criterion.

TABLE 1

| The reaction temperature and the holding time according to Examples 1-5. | | | | | | | | | |
|---|---|---|---|---|---|---|---|---|---|
| Ex. | | | Reaction temperature, | Reaction | Average molecular weight of the | Elemental analysis data, % | | | |
| No. | n | m | ° C. | time, h | product, formula | C | H | N | Cl |
| 1 | 10 | 1 | 190 | 0.5 | 1885, $C_{71}H_{156}Cl_{11}N_{34}$ | 45.24 | 8.93 | 25.26 | 20.69 |
| 2 | 5 | 2 | 190 | 0.75 | 1979, $C_{72}H_{171}Cl_{12}N_{37}$ | 43.70 | 8.71 | 26.19 | 21.50 |
| 3 | 10 | 2 | 190 | 1.5 | 3753, $C_{142}H_{309}Cl_{22}N_{67}$ | 45.45 | 8.89 | 25.01 | 21.78 |
| 4 | 10 | 5 | 200 | 2.0 | 9357, $C_{355}H_{823}Cl_{55}N_{166}$ | 45.57 | 8.87 | 24.85 | 20.84 |
| 5 | 15 | 10 | 210 | 4.0 | 27571, $C_{1060}H_{2443}Cl_{160}N_{481}$ | 46.18 | 8.93 | 24.44 | 20.57 |

TABLE 2

Results of evaluation of hemostatic activity for the
change of the bleeding intensity as per Example 1.1.

| | Relative intensity of bleeding from liver wounds, mg/min | |
|---|---|---|
| Group | Before application | 180 seconds after application |
| Prototype (iron subsulphate) | 1326.4 +/− 128.5 | 652.6 +/− 108.2 |
| The claimed substance 0.5% | 1298.2 +/− 131.4 | 367.1 +/− 48.4 |
| The claimed substance 1.0% | 1305.7 +/− 118.7 | 328.5 +/− 51.2 |

TABLE 3

Results of evaluation of hemostatic activity for the
change of the bleeding intensity as per Example 1.2.

| | Relative intensity of bleeding from liver wounds, mg/min | |
|---|---|---|
| Group | Before application | 180 seconds after application |
| Cotton swab | 1384.3 +/− 132.0 | 1154.6 +/− 99.4 |
| Cotton swab impregnated with iron subsulphate | 1384.3 +/− 132.0 | 589.5 +/− 65.4 |
| Cotton swab impregnated with the the claimed substance 0.01% | 1384.3 +/− 132.0 | 488.1 +/− 55.7 |
| Cotton swab impregnated with the the claimed substance 0.5% | 1384.3 +/− 132.0 | 344.2 +/− 37.9 |
| Cotton swab impregnated with the the claimed substance 1% | 1384.3 +/− 132.0 | 332.3 +/− 42.1 |
| Cotton swab impregnated with the the claimed substance 10% | 1384.3 +/− 132.0 | 335.2 +/− 24.8 |

TABLE 4

Results of evaluation of hemostatic activity for the
change of the bleeding intensity as per Example 1.3.

| | Relative intensity of bleeding, mg/min | |
|---|---|---|
| Group | Before application | 60 seconds after use |
| Resorbable suture material (catgut) | 217.5 +/− 29.6 | 108.7 +/− 17.5 |
| Resorbable suture material (catgut) impregnated with the claimed substance | 217.5 +/− 29.6 | 29.3 +/− 6.7 |
| Non-resorbable suture material (nylon) | 217.5 +/− 29.6 | 94.2 +/− 10.2 |
| Non-resorbable suture material (nylon) impregnated with the claimed substance | 217.5 +/− 29.6 | 31.8 +/− 4.9 |

TABLE 5

Relative bleeding intensity while using a hemostatic collagen
sponge impregnated with the claimed substance.

| | Relative intensity of bleeding, mg/min | |
|---|---|---|
| Group | Before application | 180 seconds after application |
| collagen hemostatic sponge | 1421.6 +/− 125.8 | 1003 +/− 87.5 |
| collagen hemostatic sponge impregnated with iron subsulphate | 1421.6 +/− 125.8 | 514.9 +/− 47.6 |

TABLE 5-continued

Relative bleeding intensity while using a hemostatic collagen
sponge impregnated with the claimed substance.

| | Relative intensity of bleeding, mg/min | |
|---|---|---|
| Group | Before application | 180 seconds after application |
| collagen hemostatic sponge impregnated with the claimed substance 0.01 | 1421.6 +/− 125.8 | 396.6 +/− 42.5 |
| collagen hemostatic sponge impregnated with the claimed substance 0.5% | 1421.6 +/− 125.8 | 325.6 +/− 34.7 |
| collagen hemostatic sponge impregnated with the claimed substance 1% | 1421.6 +/− 125.8 | 225.8 +/− 30.4 |
| collagen hemostatic sponge impregnated with the claimed substance 10% | 1421.6 +/− 125.8 | 121.4 +/− 10.5 |

TABLE 6

Relative bleeding intensity while using a fibrin
film impregnated with the claimed substance.

| | Relative intensity of bleeding, mg/min | |
|---|---|---|
| Group | Before application | 180 seconds after application |
| fibrin film + iron subsulphate | 1395.1 +/− 98.4 | 987.3 +/− 94.2 |
| fibrin film impregnated with the claimed substance 0.01% | 1395.1 +/− 98.4 | 456.3 +/− 36.2 |
| fibrin film impregnated with the claimed substance 0.5% | 1395.1 +/− 98.4 | 325.6 +/− 28.5 |
| fibrin film impregnated with the claimed substance 1% | 1395.1 +/− 98.4 | 245.4 +/− 33.7 |
| fibrin film impregnated with the claimed substance 10% | 1395.1 +/− 98.4 | 165.1 +/− 14.6 |

TABLE 7

Relative bleeding intensity while using комбинированной губки
a sponge containing fibrinogen and
thrombin and impregnated with the claimed substance.

| | Relative intensity of bleeding, mg/min | |
|---|---|---|
| Group | Before application | 180 seconds after application |
| комбинированная губка containing fibrinogen and thrombin + iron subsulphate | 1283.0 +/− 85.5 | 934.2 +/− 74.2 |
| комбинированная губка, containing fibrinogen and thrombin, and impregnated with the claimed substance 0.01% | 1283.0 +/− 85.5 | 434.5 +/− 48.0 |
| комбинированная губка, containing fibrinogen and thrombin, and impregnated with the claimed substance 0.5% | 1283.0 +/− 85.5 | 327.1 +/− 28.6 |
| комбинированная губка, containing fibrinogen and thrombin, and impregnated with the claimed substance 1% | 1283.0 +/− 85.5 | 249.3 +/− 25.4 |
| комбинированная губка, containing fibrinogen and thrombin, and impregnated with the claimed substance 10% | 1283.0 +/− 85.5 | 189.2 +/− 32.7 |

TABLE 8

Relative bleeding intensity while using a polysaccharide hemostatic system with the addition of the claimed substance.

| Group | Relative intensity of bleeding, mg/min | |
|---|---|---|
| | Before application | 120 seconds after application |
| polysaccharide hemostatic system | 1248.0 +/− 109.2 | 832.2 +/− 63.5 |
| polysaccharide hemostatic system with the addition of the claimed substance 0.01% | 1248.0 +/− 109.2 | 425.4 +/− 52.2 |
| polysaccharide hemostatic system with the addition of the claimed substance 0.5% | 1248.0 +/− 109.2 | 224.2 +/− 37.9 |
| polysaccharide hemostatic system with the addition of the claimed substance 1% | 1248.0 +/− 109.2 | 201.7 +/− 25.1 |
| polysaccharide hemostatic system with the addition of the claimed substance 10% | 1248.0 +/− 109.2 | 185.6 +/− 19.8 |

TABLE 9

Relative bleeding intensity while using a cellulose-based hemostatic material with the addition of the claimed substance.

| Group | Relative intensity of bleeding, mg/min | |
|---|---|---|
| | Before application | 120 seconds after application |
| cellulose-based hemostatic material | 1425.9 +/− 153.2 | 1154.6 +/− 99.4 |
| cellulose-based hemostatic material with the addition of the claimed substance 0.01% | 1425.9 +/− 153.2 | 434.7 +/− 65.2 |
| cellulose-based hemostatic material with the addition of the claimed substance 0.5% | 1425.9 +/− 153.2 | 274.0 +/− 37.9 |
| cellulose-based hemostatic material with the addition of the claimed substance 1% | 1425.9 +/− 153.2 | 282.6 +/− 32.1 |
| cellulose-based hemostatic material with the addition of the claimed substance 10% | 1425.9 +/− 153.2 | 123.0 +/− 20.1 |

TABLE 10

Relative intensity of bleeding

| Group | Relative intensity of bleeding, mg/min | |
|---|---|---|
| | Before application | 120 seconds after application |
| aluminum sulphate based gel | 1437.5 +/− 141.6 | 856.4 +/− 83.2 |
| aluminum sulphate based gel with the addition of the claimed substance 0.01% | 1437.5 +/− 141.6 | 545.2 +/− 55.4 |
| aluminum sulphate based gel with the addition of the claimed substance 0.5% | 1437.5 +/− 141.6 | 388.2 +/− 32.3 |
| aluminum sulphate based gel with the addition of the claimed substance 1% | 1437.5 +/− 141.6 | 234.8 +/− 38.0 |
| aluminum sulphate based gel with the addition of the claimed substance 10% | 1437.5 +/− 141.6 | 224.2 +/− 34.9 |
| Silver nitrate solution (1:200) | 1437.5 +/− 141.6 | 1035.7 +/− 119.0 |
| Silver nitrate solution (1:200) with the addition of the claimed substance 0.01% | 1437.5 +/− 141.6 | 524.6 +/− 58.4 |
| Silver nitrate solution (1:200) with the addition of the claimed substance 0.5% | 1437.5 +/− 141.6 | 362.1 +/− 35.7 |
| Silver nitrate solution (1:200) with the addition of the claimed substance 1% | 1437.5 +/− 141.6 | 287.3 +/− 32.6 |
| Silver nitrate solution (1:200) with the addition of the claimed substance 10% | 1437.5 +/− 141.6 | 211.5 +/− 23.9 |

TABLE 11

Relative bleeding intensity while using a retraction cord with the addition of the claimed substance.

| Group | Relative intensity of bleeding, mg/min | |
|---|---|---|
| | Before application | 120 seconds after application |
| Retraction cord | 475.2 +/− 38.0 | 226.4 +/− 25.6 |
| Retraction cord impregnated with a solution of iron subsulphate | 475.2 +/− 38.0 | 152.2 +/− 12.2 |
| Retraction cord impregnated with 0.01% solution of the claimed substance | 475.2 +/− 38.0 | 58.6 +/− 5.3 |
| Retraction cord impregnated with 0.5% solution of the claimed substance | 475.2 +/− 38.0 | 32.9 +/− 3.9 |
| Retraction cord impregnated with 1% solution of the claimed substance | 475.2 +/− 38.0 | 29.3 +/− 2.4 |
| Retraction cord impregnated with 10% solution of the claimed substance | 475.2 +/− 38.0 | 23.4 +/− 4.5 |

TABLE 12

Change of the bleeding arrest time while using a bandaging material or a plaster, impregnated with the claimed substance.

| Group | Ultimate bleeding arrest time, sec |
|---|---|
| Bandaging material | 158 |
| Bandaging material with the addition of the claimed substance 0.01% | 64 |
| Bandaging material with the addition of the claimed substance 0.5% | 21 |
| Bandaging material with the addition of the claimed substance 1% | 20 |
| Bandaging material with the addition of the claimed substance 10% | 22 |
| Plaster | 134 |
| Plaster with the addition of the claimed substance 0.01% | 58 |
| Plaster with the addition of the claimed substance 0.5% | 24 |
| Plaster with the addition of the claimed substance 1% | 21 |
| Plaster with the addition of the claimed substance 10% | 19 |

TABLE 13

Change in the pain sensation intensity in soft corns.

| | Pain sensation intensity on a visual analog scale | | |
|---|---|---|---|
| Group | Before treatment | In 1 minute | In 2 days |
| Iron subsulphate solution | 4.2 +/− 0.2 | 4.5 +/− 0.4 | 3.9 +/− 0.3 |
| 0.01% solution of the preparation | 4.2 +/− 0.2 | 2.3 +/− 0.2 | 0 |
| 0.5% solution of the preparation | 4.2 +/− 0.2 | 1.4 +/− 0.1 | 0 |
| 1.0% solution of the preparation | 4.2 +/− 0.2 | 1.1 +/− 0.2 | 0 |
| 10.0% solution of the preparation | 4.2 +/− 0.2 | 1.2 +/− 0.3 | 0 |

TABLE 14

Change in the itch intensity in genital candidiasis.

| | Itch intensity on the Itch Severity Score (ISS) scale, points* | |
|---|---|---|
| Group | 1 minute after application of the preparation | In 5 days (for daily administration) |
| Without treatment | 4 | 6 |
| Prototype (iron subsulphate) | 4 | 5 |
| 0.01% solution of the claimed substance | 2 | 0 |
| 0.5% solution of the claimed substance | 1 | 0 |
| 1.0% solution of the claimed substance | 1 | 0 |
| 10.0% solution of the claimed substance | 1 | 0 |
| Vaginal suppositories with the addition of the claimed substance | 1 | 0 |

*The specified number has been rounded to the higher value.

TABLE 15

Change in the pain sensation intensity.

| | Pain sensation intensity on a visual analog scale | | |
|---|---|---|---|
| Group | Before treatment | 1 minute after application of the preparation | In 2 days (for dayly administeration) |
| Solcoseryl adhesive paste (reference) | 5.3 +/− 0.4 | 5.2 +/− 0.2 | 3.1 +/− 0.3 |
| Adhesive paste containing 10.0% of the preparation | 5.3 +/− 0.4 | 2.4 +/− 0.3 | 0 |
| Adhesive paste containing 0.5% of the preparation | 5.3 +/− 0.4 | 1.2 +/− 0.2 | 0 |
| Adhesive paste containing 1.0% of the preparation | 5.3 +/− 0.4 | 0.7 +/− 0.2 | 0 |
| Adhesive paste containing 10.0% of the preparation | 5.3 +/− 0.4 | 0.8 +/− 0.1 | 0 |

TABLE 16

Change in the intensity of indications in patients with chronic hemorrhoids*.

| | Before treatment (in points) | | | 3 days after beginning of the treatment (in points) | | | 7 days after beginning of the treatment (in points) | | |
|---|---|---|---|---|---|---|---|---|---|
| Group | Pain | Anal itch | Hemorrhage | Pain | Anal itch | Hemorrhage | Pain | Anal itch | Hemorrhage |
| prototype - supositories with iron subsulphate | 3 | 3 | 3 | 3 | 3 | 2 | 3 | 3 | 1 |
| supositories with hemostatic and analgesic effect | 3 | 3 | 3 | 3 | 2 | 2 | 1 | 1 | 1 |
| supositories with the claimed preparation | 3 | 3 | 3 | 1 | 1 | 1 | 0 | 0 | 0 |

*The specified number has been rounded to the higher value.

TABLE 17

Change in itch intensity in patients with skin diseases.

Itch intensity on the Itch Severity Score (ISS) scale, points*

| Group 1 | Before treatment | | | | 1 minute after application of the preparation | | | |
|---|---|---|---|---|---|---|---|---|
| | atopic dermatitis 2 | eczema 3 | neurodermatitis 4 | psoriasis 5 | atopic dermatitis 6 | eczema 7 | neurodermatitis 8 | psoriasis 9 |
| Without treatment | 6 | 6 | 8 | 8 | 6 | 6 | 8 | 8 |
| 0.01% solution of the claimed substance | 6 | 6 | 8 | 8 | 4 | 4 | 4 | 6 |
| 0.5% solution of the claimed substance | 6 | 6 | 8 | 8 | 3 | 3 | 3 | 6 |
| 1.0% solution of the claimed substance | 6 | 6 | 8 | 8 | 2 | 2 | 2 | 6 |
| 10.0% solution of the claimed substance | 6 | 6 | 8 | 8 | 2 | 2 | 3 | 5 |
| 0.01% cream with the claimed substance | 6 | 6 | 8 | 8 | 4 | 4 | 4 | 6 |
| 0.5% cream with the claimed substance | 6 | 6 | 8 | 8 | 3 | 2 | 3 | 4 |
| 10% cream with the claimed substance | 6 | 6 | 8 | 8 | 2 | 2 | 2 | 4 |
| 0.01% gel with the claimed substance | 6 | 6 | 8 | 8 | 4 | 4 | 4 | 6 |
| 0.5% gel with the claimed substance | 6 | 6 | 8 | 8 | 3 | 2 | 3 | 4 |
| 5% gel with the claimed substance | 6 | 6 | 8 | 8 | 2 | 2 | 2 | 4 |
| 0.01% ointment with the claimed substance | 6 | 6 | 8 | 8 | 4 | 4 | 4 | 6 |
| 0.5% ointment with the claimed substance | 6 | 6 | 8 | 8 | 3 | 2 | 3 | 4 |
| 5% ointment with the claimed substance | 6 | 6 | 8 | 8 | 2 | 2 | 2 | 4 |
| application strips with the claimed substance, 0.01% | 6 | 6 | 8 | 8 | 4 | 4 | 4 | 6 |
| application strips with the claimed substance, 0.5% | 6 | 6 | 8 | 8 | 3 | 2 | 3 | 4 |
| application strips with the claimed substance, 10.0% | 6 | 6 | 8 | 8 | 2 | 2 | 2 | 4 |

TABLE 17-continued

Change in itch intensity in patients with skin diseases.

| Group 1 | | Itch intensity on the Itch Severity Score (ISS) scale, points* In 5 days (for dayly administeration) | | | |
|---|---|---|---|---|---|
| | | atopic dermatitis 10 | eczema 11 | neurodermatitis 12 | psoriasis 13 |
| | Without treatment | 6 | 6 | 8 | 8 |
| | 0.01% solution of the claimed substance | 2 | 3 | 3 | 4 |
| | 0.5% solution of the claimed substance | 1 | 2 | 2 | 3 |
| | 1.0% solution of the claimed substance | 1 | 1 | 1 | 1 |
| | 10.0% solution of the claimed substance | 1 | 1 | 1 | 1 |
| | 0.01% cream with the claimed substance | 2 | 3 | 3 | 3 |
| | 0.5% cream with the claimed substance | 1 | 1 | 1 | 2 |
| | 10% cream with the claimed substance | 1 | 1 | 1 | 1 |
| | 0.01% gel with the claimed substance | 2 | 3 | 3 | 3 |
| | 0.5% gel with the claimed substance | 1 | 1 | 1 | 2 |
| | 5% gel with the claimed substance | 1 | 1 | 1 | 1 |
| | 0.01% ointment with the claimed substance | 2 | 3 | 3 | 3 |
| | 0.5% ointment with the claimed substance | 1 | 1 | 1 | 2 |
| | 5% ointment with the claimed substance | 1 | 1 | 1 | 1 |
| | application strips with the claimed substance, 0.01% | 2 | 3 | 3 | 3 |
| | application strips with the claimed substance, 0.5% | 1 | 1 | 1 | 2 |
| | application strips with the claimed substance, 10.0% | 1 | 1 | 1 | 1 |

TABLE 18

Change in the pain sensation intensity in patients with burns.

Pain sensation intensity on a visual analog scale

| Group | Before treatment | 1 minute after application of the preparation | In 5 days (for daily administration) |
|---|---|---|---|
| Collagen dressing (reference) | 7.9+/0.6 | 8.4+/0.5 | 4.4 +/− 0.6 |
| Hydrogel (reference) | 7.9+/0.6 | 7.3+/0.2 | 3.6 +/− 0.5 |
| 0.01% solution of the claimed substance | 7.9+/0.6 | 4.5+/0.5 | 2.2 +/− 0.3 |
| 0.5% solution of the claimed substance | 7.9+/0.6 | 2.5+/0.3 | 1.3 +/− 0.2 |
| 1.0% solution of the claimed substance | 7.9+/0.6 | 2.3+/0.5 | 1.2 +/− 0.1 |
| 10.0% solution of the claimed substance | 7.9+/0.6 | 2.2+/0.3 | 1.4 +/− 0.5 |

TABLE 19

Change in the pain sensation intensity.

Pain sensation intensity on a visual analog scale

| Group | Before treatment | 1 minute after application of the preparation | In 2 days (for dayly administeration) |
|---|---|---|---|
| Oxybuprocaine (reference) | 7.6 +/− 0.8 | 2.2 +/− 0.4 | 0.5 +/− 0.1 |
| 0.01% solution of the claimed substance | 7.6 +/− 0.8 | 4.5 +/− 0.3 | 2.0 +/− 0.2 |
| 0.5% solution of the claimed substance | 7.6 +/− 0.8 | 3.0 +/− 0.2 | 1.1 +/− 0.2 |
| 1.0% solution of the claimed substance | 7.6 +/− 0.8 | 2.9 +/− 0.3 | 1.0 +/− 0.1 |
| 10.0% solution of the claimed substance | 7.6 +/− 0.8 | 3.1 +/− 0.4 | 0.9 +/− 0.1 |

TABLE 20

Change in the pain sensation intensity in angina.

Pain sensation intensity on a visual analog scale

| Group | Before treatment | 1 minute after application of the preparation | In 2 days (for dayly administeration) |
|---|---|---|---|
| Reference | 6.9 +/− 0.7 | 6.6 +/− 0.6 | 7.4 +/− 0.4 |
| 0.01% solution of the claimed substance | 6.9 +/− 0.7 | 4.3 +/− 0.4 | 0.7 +/− 0.2 |
| 1.0% solution of the claimed substance | 6.9 +/− 0.7 | 2.1 +/− 0.3 | 0.2 +/− 0.2 |
| 10.0% solution of the claimed substance | 6.9 +/− 0.7 | 2.0 +/− 0.4 | 0.3 +/− 0.1 |

TABLE 21

Change of the ultimate bleeding arrest time after removal of the pulp.

| Group | Ultimate bleeding arrest time, sec |
|---|---|
| 0.9% sodium chloride | 58 |
| 0.01% solution of the claimed substance | 18 |
| 0.5% solution of the claimed substance | 12 |
| 1% solution of the claimed substance | 8 |
| 10% solution of the claimed substance | 9 |
| Paper point | 44 |
| Paper point impregnated with the claimed substance | 8 |
| Cotton swab | 32 |
| Cotton swab impregnated with the claimed substance | 9 |

TABLE 22

Change in the pain sensation intensity during treatment of acute exacerbations of chronic pulpitis.

Pain sensation intensity on a visual analog scale

| Group | Before treatment | In 24 hrs | In 36 hrs |
|---|---|---|---|
| Reference (sealer) | 3.4 +/− 0.2 | 3.2 +/− 0.5 | 2.3 +/− 0.4 |
| Sealer with the addition of the claimed substance 0.01% | 3.4 +/− 0.2 | 1.7 +/− 0.3 | 0.3 +/− 0.1 |
| Sealer with the addition of the claimed substance 1.0% | 3.4 +/− 0.2 | 0.8 +/− 0.2 | 0.2 +/− 0.2 |
| Sealer with the addition of the claimed substance 2.0% | 3.4 +/− 0.2 | 0.9 +/− 0.1 | 0.2 +/− 0.1 |

TABLE 23

Change in the pain sensation intensity in inflammatory diseases of the paradentium and gums.

Pain sensation intensity on a visual analog scale

| Group | Before treatment | In 1 minute | In 2 days |
|---|---|---|---|
| Reference | 6.3 +/− 0.5 | 6.2 +/− 0.4 | 5.2 +/− 0.3 |
| 0.01% solution of the claimed substance | 6.3 +/− 0.5 | 3.2 +/− 0.2 | 0.2 +/− 0.1 |
| 1.0% solution of the claimed substance | 6.3 +/− 0.5 | 2.3 +/− 0.1 | 0.3 +/− 0.2 |
| 10.0% solution of the claimed substance | 6.3 +/− 0.5 | 2.1 +/− 0.3 | 0.2 +/− 0.2 |
| 0.01% gel of the claimed substance | 6.3 +/− 0.5 | 3.0 +/− 0.4 | 0.2 +/− 0.1 |
| 1.0% gel of the claimed substance | 6.3 +/− 0.5 | 2.2 +/− 0.4 | 0.1 +/− 0.1 |
| 10.0% gel of the claimed substance | 6.3 +/− 0.5 | 1.9 +/− 0.2 | 0.3 +/− 0.3 |
| A chip with slow release of the claimed substance, 0.01% | 6.3 +/− 0.5 | 4.5 +/− 0.6 | 0.4 +/− 0.2 |
| A chip with slow release of the claimed substance, 1.0% | 6.3 +/− 0.5 | 4.2 +/− 0.2 | 0.3 +/− 0.1 |
| A chip with slow release of the claimed substance, 10.0% | 6.3 +/− 0.5 | 3.5 +/− 0.3 | 0.2 +/− 0.2 |

TABLE 24

Change in the pain sensation intensity.

| | Pain sensation intensity on a visual analog scale | | |
|---|---|---|---|
| Group | Before treatment | In 1 minute | In 5 days |
| Iron subsulphate solution | 4.2 +/− 0.7 | 4.4 +/− 0.7 | 4.2 +/− 0.7 |
| 0.01% solution of the claimed substance | 4.2 +/− 0.7 | 2.5 +/− 0.4 | 2.2 +/− 0.7 |
| 1.0% solution of the claimed substance | 4.2 +/− 0.7 | 2.3 +/− 0.3 | 2.1 +/− 0.7 |
| Amiloride + 1.0% solution of the claimed substance | 4.2 +/− 0.7 | 1.3 +/− 0.1 | 0.1 +/− 0.1 |
| Atropine + 1.0% solution of the claimed substance | 4.2 +/− 0.7 | 1.2 +/− 0.2 | 0.4 +/− 0.2 |
| Corticosteroids + 1.0% solution of the claimed substance | 4.2 +/− 0.7 | 0.9 +/− 0.3 | 0.2 +/− 0.1 |
| N-acetylcysteine + 1.0% solution of the claimed substance | 4.2 +/− 0.7 | 0.8 +/− 0.1 | 0.3 +/− 0.1 |
| Ambroxol + 1.0% solution of the claimed substance | 4.2 +/− 0.7 | 1.1 +/− 0.2 | 0.3 +/− 0.2 |

TABLE 25

Clinical manifestations.

| | Presence of bloody sputum | | |
|---|---|---|---|
| Group | Before treatment | In 1 minute | In 5 days |
| Control (iron subsulphate) | ++++ | +++ | ++ |
| 0.01% solution of the claimed substance | ++++ | ++ | ++ |
| 1.0% solution of the claimed substance | ++++ | ++ | + |

TABLE 26

Change in the pain sensation intensity in inflammatory diseases of musculoskeletal system.

| | Pain sensation intensity on a visual analog scale | | |
|---|---|---|---|
| Group | Before treatment | In 1 hr | In 24 hrs |
| A 0.9% sodium chloride solution | 6.5 +/− 0.8 | 6.8 +/− 0.6 | 7.1 +/− 0.9 |
| 0.01% solution of the claimed substance | 6.5 +/− 0.8 | 5.2 +/− 0.4 | 3.3 +/− 0.2 |
| 0.5% solution of the claimed substance | 6.5 +/− 0.8 | 4.3 +/− 0.5 | 1.4 +/− 0.4 |
| 1.0% solution of the claimed substance | 6.5 +/− 0.8 | 2.1 +/− 0.3 | 0.8 +/− 0.3 |
| 5.0% solution of the claimed substance | 6.5 +/− 0.8 | 2.0 +/− 0.3 | 1.1 +/− 0.2 |

TABLE 27

Change in the pain sensation intensity in gout.

| | Pain sensation intensity on a visual analog scale | | |
|---|---|---|---|
| Group | Before treatment | In 1 hr | In 7 days |
| Reference (0.9% NaCl solution) | 5.4 +/− 0.6 | 5.6 +/− 0.5 | 5.3 +/− 0.6 |
| 0.01% solution of the claimed substance | 5.4 +/− 0.6 | 4.1 +/− 0.4 | 1.6 +/− 0.2 |
| 0.5% solution of the claimed substance | 5.4 +/− 0.6 | 4.2 +/− 0.3 | 1.4 +/− 0.1 |
| 1.0% solution of the claimed substance | 5.4 +/− 0.6 | 3.6 +/− 0.2 | 0.6 +/− 0.3 |
| 2.0% solution of the claimed substance | 5.4 +/− 0.6 | 3.2 +/− 0.2 | 0.5 +/− 0.2 |

TABLE 28

Change in the pain sensation intensity.

| | Pain sensation intensity on a visual analog scale | | |
|---|---|---|---|
| Group | Before treatment | In 1 minute | In 10 minute |
| Reference (Diclofenac solution) | 6.9 +/− 0.8 | 7.1 +/− 0.5 | 7.2 +/− 0.6 |
| 0.01% solution of the claimed substance | 6.9 +/− 0.8 | 2.1 +/− 0.3 | 1.6 +/− 0.2 |
| 0.5% solution of the claimed substance | 6.9 +/− 0.8 | 1.2 +/− 0.5 | 0.2 +/− 0.1 |
| 1.0% solution of the claimed substance | 6.9 +/− 0.8 | 0.8 +/− 0.2 | 0.2 +/− 0.1 |
| 2.0% solution of the claimed substance | 6.9 +/− 0.8 | 1.1 +/− 0.1 | 0.4 +/− .2 |

TABLE 29

Change in the pain sensation intensity.

| | Pain sensation intensity on a visual analog scale | | |
|---|---|---|---|
| Group | Before treatment | In 1 minute | In 10 minute |
| Prototype (iron subsulphate) | 4.7 +/− 0.5 | 4.5 +/− 0.4 | 4.6 +/− 0.5 |
| 0.01% solution of the claimed substance | 4.7 +/− 0.5 | 2.5 +/− 0.2 | 0.4 +/− 0.2 |
| 1.0% solution of the claimed substance | 4.7 +/− 0.5 | 1.3 +/− 0.2 | 0.2 +/− 0.2 |

TABLE 30

Change in the bleeding intensity.

| | Pain sensation intensity on a visual analog scale | | |
|---|---|---|---|
| Group | Before treatment | In 1 minute | In 10 minute |
| Prototype (iron subsulphate) | ++++ | ++ | − |
| 0.01% solution of the claimed substance | ++++ | ++ | − |
| 1.0% solution of the claimed substance | ++++ | + | − |

The invention claimed is:

1. A method of reducing bleeding and/or pain in a subject in need thereof, comprising administering to the subject a compound of Formula:

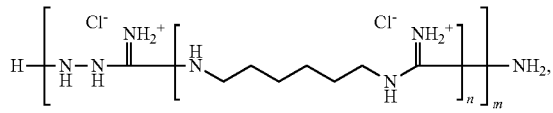

wherein: n is 1-20, m is 1-10, and n×m≥8.

2. The method of claim 1, wherein n is 5 and m is 2.
3. The method of claim 1, wherein n is 10 and m is 2.
4. The method of claim 1, wherein n is 10 and m is 5.
5. The method of claim 1, wherein n is 15 and m is 10.
6. The method of claim 1, wherein n is 10 and m is 1.
7. The method of claim 1, wherein method further provides relief for itching sensation.
8. The method of claim 1, wherein the method involves applying the compound to a wound surface.
9. The method of claim 1, wherein the compound is provided in the form of an aqueous solution.
10. The method of claim 9, wherein the aqueous solution has a concentration of about 0.01 to about 10% of the compound.
11. The method of claim 1, wherein the compound is impregnated in a material used for bleeding arrest.
12. The method of claim 11, wherein the impregnated material comprises, a gauze, a swab, a suture material, a bandage material, a collagen hemostatic sponge, a fibrin film, a polymer sealer, a polysaccharide material comprising cellulose, an aluminum sulfate gel, a silver nitrate solution, and iron sulfate solution, a plaster, a retraction cord, a vaginal or rectal suppository, a microchip, a catheter, or an adhesive paste.
13. The method of claim 1, wherein the method is for treating bleeding associated with liver wounds, dental treatment, eye trauma, genital candidiasis, hemorrhoids, dermatitis, eczema, neurodermatitis, psoriasis, burns, angina, respiratory disease, a skin disease, diseases of the musculoskeletal system, gout, or digestive system pathologies.
14. The method of claim 13, wherein the dental treatment comprises endodontic treatment or inflammatory diseases of the paradentium or gums.
15. The method of claim 13, wherein the respiratory disease comprises chronic obstructive pulmonary disease, pneumonia, cystic fibrosis, or tuberculosis.
16. The method of claim 13, wherein the disease of the musculoskeletal system comprises arthritis, rheumatism, or osteochondrosis.
17. A hemostatic material comprising a compound of Formula:

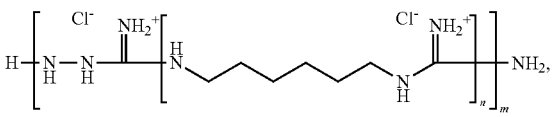

wherein: n is 1-20, m is 1-10, and n×m≥8, wherein the compound is impregnated in the hemostatic material.

18. The hemostatic material of claim 17, wherein the impregnated material comprising a gauze, a swab, a suture material, a bandage material, a collagen hemostatic sponge, a fibrin film, a polymer sealer, a polysaccharide material comprising cellulose, an aluminum sulfate gel, a silver nitrate solution, and iron sulfate solution, a plaster, a retraction cord, a vaginal or rectal suppository, a microchip, a catheter, or an adhesive paste.
19. The hemostatic material of claim 17, comprising a cream or gel.
20. The hemostatic material of claim 17, wherein the compound is applied to the surface of a catheter.

* * * * *